United States Patent
Xie et al.

(10) Patent No.: US 11,406,821 B2
(45) Date of Patent: Aug. 9, 2022

(54) FUNCTIONAL ELECTRICAL STIMULATION THERAPEUTIC APPARATUS FOR FOOT DROP

(71) Applicant: Shenzhen XFT Medical Limited, Shenzhen (CN)

(72) Inventors: Chunhu Xie, Shenzhen (CN); Chang Liu, Shenzhen (CN)

(73) Assignee: Shenzhen XFT Medical Limited

( * ) Notice: Subject to any disclaimer, the term of this patent is extended or adjusted under 35 U.S.C. 154(b) by 220 days.

(21) Appl. No.: 16/611,740

(22) PCT Filed: Aug. 31, 2018

(86) PCT No.: PCT/CN2018/103440
§ 371 (c)(1),
(2) Date: Nov. 7, 2019

(87) PCT Pub. No.: WO2020/037706
PCT Pub. Date: Feb. 27, 2020

(65) Prior Publication Data
US 2021/0330969 A1    Oct. 28, 2021

(30) Foreign Application Priority Data
Aug. 24, 2018 (CN) .......................... 201810973798.6

(51) Int. Cl.
*A61N 1/36* (2006.01)
*A61N 1/04* (2006.01)
*A61N 1/372* (2006.01)

(52) U.S. Cl.
CPC ....... *A61N 1/36003* (2013.01); *A61N 1/0456* (2013.01); *A61N 1/3603* (2017.08); *A61N 1/37223* (2013.01)

(58) Field of Classification Search
CPC .. A61N 1/0404; A61N 1/0456; A61N 1/0472; A61N 1/0484; A61N 1/22;
(Continued)

(56) References Cited

U.S. PATENT DOCUMENTS

| 2015/0335288 A1* | 11/2015 | Toth | A61B 5/6833 600/373 |
|---|---|---|---|
| 2016/0121099 A1* | 5/2016 | Kiani | A61N 1/3603 607/48 |

(Continued)

FOREIGN PATENT DOCUMENTS

| CN | 202427054 | 9/2012 |
|---|---|---|
| CN | 203227204 | 10/2013 |

(Continued)

OTHER PUBLICATIONS

International Search Report for WO2020037706.
Written Opinion of the International Searching Authority of WO2020037706.

*Primary Examiner* — Carl H Layno
*Assistant Examiner* — Jane C Kalinock
(74) *Attorney, Agent, or Firm* — David G. Rosenbaum

(57) ABSTRACT

An integrated functional electrical stimulation therapeutic apparatus for foot drop based on a sequence of electrodes is provided, including an upper casing, a waterproof ring, a control circuit, a lower casing, a support molded integrally with the lower casing, a sequence of small electrodes, and a large electrode; wherein the sequence of small electrodes and the large electrode are embedded in surfaces of the lower casing and the support by using an in-mold injection process, and the sequence of small electrodes and the large electrode are stainless steel metal electrodes. An integrated waterproof design is used in the above therapeutic apparatus.

18 Claims, 6 Drawing Sheets

(58) Field of Classification Search
CPC .. A61N 1/321; A61N 1/36003; A61N 1/3603; A61N 1/37223; A61F 5/0113
USPC .......................................... 607/49, 144, 149
See application file for complete search history.

(56) References Cited

U.S. PATENT DOCUMENTS

| | | | |
|---|---|---|---|
| 2018/0200514 A1* | 7/2018 | Druke | A61B 5/6825 |
| 2018/0318583 A1* | 11/2018 | McBride | A61B 5/6828 |
| 2019/0134393 A1* | 5/2019 | Wong | A61N 1/36025 |

FOREIGN PATENT DOCUMENTS

| | | |
|---|---|---|
| CN | 204233610 | 4/2015 |
| CN | 107335140 | 11/2017 |
| WO | 2015188889 A1 | 12/2015 |

* cited by examiner

FUNCTIONAL ELECTRICAL STIMULATION THERAPEUTIC APPARATUS FOR FOOT DROP

CROSS-REFERENCE TO RELATED APPLICATIONS

The present application claims priority from and is a National Phase of PCT application serial no. PCT/CN2018/103440, filed Aug. 31, 2018, which claims priority to Chinese patent application serial no. CN 201810973798.6, filed Aug. 24, 2018, herein incorporated by reference in their entireties.

BACKGROUND

Technical Field

The present disclosure pertains to the field of electrotherapy equipment, and in particular relates to an integrated functional electrical stimulation therapeutic apparatus for foot drop based on a sequence of electrodes (or sequential electrodes).

Background Art

Foot drop is one of the signs of orthopedic surgery. When a patient is seated, the two lower limbs are naturally overhanging. If a foot is found to be in the plantar flexion position and is totally incapable of active dorsiflexion, inversion, or eversion, the patient suffers from foot drop. Common methods for treating foot drop include foot thermotherapy, rehabilitation exercise, acupuncture and massage, wearing of a brace, suspension of anterior tibialis and extensor digitorum longus tendon, posterior tibial tendon transfer for the treatment of foot drop, antedisplacement of gastrocnemius caput mediale and laterale, reconstruction of the extensor digitorum function, surgical resection, electrical stimulation, etc. Foot drop and foot varus are direct manifestations of lower limb dysfunction in patients with hemiplegia. Functional electrical stimulation (FES) walking assistance apparatuses are often used clinically to partially restore functional movement capabilities of the patients. Chinese Patent No. CN205460479U discloses a wearable foot drop treatment apparatus based on MEMS sensor, which is implemented with an integrated design, but which cannot solve the problem of malfunction of the treatment apparatus due to sweat or water resulting from other reasons and the problem of short service life, and also cannot solve the problem of inapplicability to different groups of people due to differences in neuromuscular groups between individuals among groups of people. Chinese Patent Publication No. CN103816613A discloses a portable anterior tibialis electrostimulator, which can be carried conveniently, but has poor waterproofness, poor applicability, and short service life. Chinese Patent Publication No. CN101947153A discloses a wearable intelligent foot drop appliance, which is designed with an integrated design, but has a complicated structure, poor waterproofness, poor applicability, and short service life. Yan Tiebin et al. ("Low-frequency Pulse Electrical Stimulation Therapeutic Apparatus for Paralysis Based on Walking Mode", Yan Tiebin et al., "China Medical Device Information", Vol. 16, No. 2, Feb. 25, 2010) discloses a low-frequency pulse electrical stimulation therapeutic apparatus for paralysis based on a walking mode, which is alleged to be applicable to different groups of people according to differences between individuals, but it actually cannot effectively solve the problem of narrow applicability due to differences in neuromuscular groups between individuals among groups of people, moreover it has a complicated design, poor waterproofness, and short service life.

The functional electrical stimulation therapeutic apparatus in the prior art does not have a waterproof function, its strap and main unit are separated and the and the strap is not durable and is to be replaced cumbersomely, its electrode pads are a hydrogel electrodes which has short lifetime and must be frequently replaced, and positions where the electrode are to be placed is also determined complicatedly. Based on the various problems existing in the functional electrical stimulation therapeutic apparatuses for foot drop in the prior art, the applicant has creatively invented an integrated functional electrical stimulation therapeutic apparatus for foot drop based on a sequence of electrodes which has high durability, simple operations and long lifetime, and is suitable for different groups of people.

SUMMARY OF THE INVENTION

In view of this, an object of the present disclosure is to provide an integrated functional electrical stimulation therapeutic apparatus for foot drop based on a sequence of electrodes which has high durability, simple operations and long lifetime, and is suitable for different groups of people.

In order to achieve the above object, the present disclosure provides a functional electrical stimulation therapeutic apparatus for foot drop, comprising an upper casing, a waterproof ring, a control circuit, a lower casing, a support molded integrally with the lower casing, a sequence of small electrodes, and a large electrode; wherein the sequence of small electrodes and the large electrode are embedded in surfaces of the lower casing and the support by using an in-mold injection process, and the sequence of small electrodes and the large electrode are stainless steel metal electrodes.

Further, the control circuit is connected with a magnetic connector, the magnetic connector is disposed in the lower casing and connected with a charging cable via a charging port of the lower casing, and the charging port is in a closed state when it is idle.

Further, the control circuit is connected with the magnetic connector via a magnetic connector circuit board.

Further, an inner surface of the upper casing has a limiting frame, a first flexible circuit board is attached in the limiting frame, a button mark is provided at a location of an outer surface of the upper casing that is corresponding to the first flexible circuit board, and the first flexible circuit board is connected with the control circuit for transmitting, to the control circuit, information on button pressing by a user.

Further, a surface of the support is provided with a wiring slot in which a second flexible circuit board having pad locations is mounted, wherein the second flexible circuit board is connected with the control circuit via the pad locations; the sequence of small electrodes have bumps respectively connected with the pad locations so as to be connected with the control circuit.

Further, the surface of the support is provided with a cover slot and a cover for flexible circuit matched with the cover slot, and the wiring slot is disposed in the cover slot.

Further, the sequence of small electrodes comprises at least six small electrodes, the plurality of small electrodes are symmetrically distributed, the large electrode has an oblong shape, each small electrode of the sequence of small electrodes has a rectangular shape, and the control circuit, the small electrodes, a human body, and the large electrode constitute an electrical stimulation loop.

Further, the surface of the lower casing and the surface of the support are coated with a soft rubber, and the soft rubber is extended to form a strap.

Further, a front end of the upper casing is provided with a lug, the strap is provided with a Velcro loop material and a Velcro hook material, wherein the Velcro loop material is fixed to an upper end of the strap by a machine sewing process, the Velcro hook material is fixed to a lower end of the strap by the machine sewing process, the strap passes through the lug and is folded back and then fixed by the Velcro, and a length by which the strap is to be folded back is adjusted and fixed by the Velcro.

Further, the strap is made of a TPE or TPU material.

Further, the large electrode can cover a junction of the common peroneal nerve, and the small electrodes can cover branches of the common peroneal nerve.

Further, a rear end of the support has a positioning point which is spaced apart from a nearest small electrode by 1 to 5 mm, and the large electrode is spaced apart from a nearest small electrode by 10 to 15 mm.

Compared with the prior art, the present disclosure has the following advantages:

1. An integrated waterproof design is used in the present disclosure, so that the electrodes and the strap are more durable and operated more simply.

2. Stainless steel electrodes are used in the present disclosure and do not need to be replaced since the stainless steel has high durability, wear resistance, as well as good electrical conductivity.

3. A sequence of electrodes is used in the present disclosure and can cover nerves and muscles of different groups of people. The methods, systems, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the methods, apparatuses, and systems, as claimed.

BRIEF DESCRIPTION OF THE DRAWINGS

In the accompanying figures, like elements are identified by like reference numerals among the several preferred embodiments of the present invention.

In order to more clearly illustrate technical solutions of embodiments of the present disclosure or of the prior art, drawings required for use in the embodiments will be described briefly below. It is apparent that the drawings in the following description are merely illustrative of some embodiments of the present disclosure. It will be understood by those of ordinary skill in the art that other drawings can also be obtained from these drawings without any inventive effort.

DETAILED DESCRIPTION OF THE INVENTION

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

The technical solutions of the embodiments of the present disclosure will be described below clearly and completely with reference to the drawings of the embodiments of the present disclosure. It is apparent that the embodiments to be described are some, but not all of the embodiments of the present disclosure. All the other embodiments obtained by those of ordinary skill in the art in light of the embodiments of the present disclosure without inventive efforts shall fall within the scope of the present disclosure as claimed.

Figure 1:
FIG. 1 is a structural schematic view of a main unit of a functional electrical stimulation therapeutic apparatus for foot drop according to an embodiment of the present disclosure.
Figure 2:
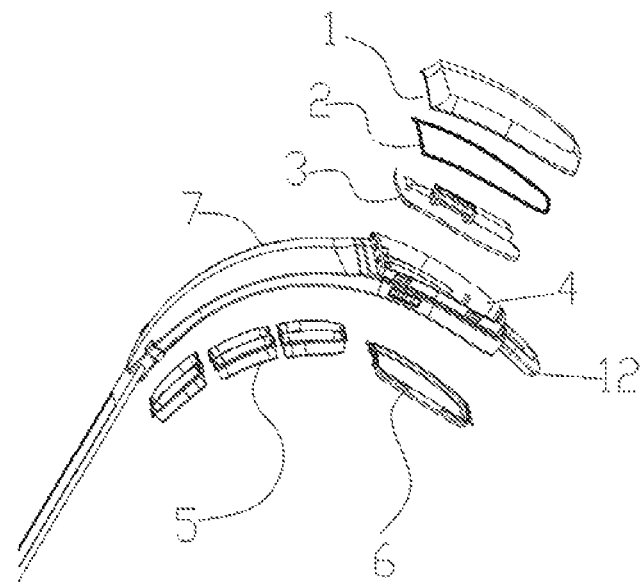
FIG. 2 is a partial enlarged view of a structural composition view of a main unit of a functional electrical stimulation therapeutic apparatus for foot drop according to an embodiment of the present disclosure.

As shown in FIG. 1 and FIG. 2, an electrical stimulation therapeutic apparatus of the present disclosure includes an upper casing 1, a waterproof ring 2, a control circuit 3, a lower casing 4, and a support molded integrally with the lower casing, a sequence of small electrodes 5, and a large electrode 6. The sequence of small electrodes 5 are embedded in the support 7 by using an in-mold injection process, and the large electrode 6 is embedded in the lower casing 4 by using an in-mold injection process.

The upper casing 1, the waterproof ring 2, and the lower casing 4 form a sealed space to achieve the waterproof function, and the control circuit 3 in the sealed space will not be soaked with a liquid such as water, so that it is ensured that electronic elements can operate normally even in a case where there is water outside, and waterproofness of the electronic circuit is achieved. The sequence of small electrodes 5 and the large electrode 6 are stainless steel metal electrodes, so that waterproofness of the electrodes is achieved. The lower casing 4, the support 7, and a strap 9 are molded integrally and coated on their surfaces with a layer of soft rubber to achieve the waterproofing function. The control circuit may detect a motion state of a leg and output an electrical stimulation to the sequence of small electrodes 5 and the large electrode 6; and the sequence of small electrodes 5 and the large electrode 6 are in contact with the skin of the leg to achieve assisted walking by the electrical stimulation. The control circuit, the sequence of small electrodes 5, the human body, and the large electrode 6 constitute an electrical stimulation circuit.

In the prior art, the electrodes and main unit (here, the main unit comprises the upper casing, the control circuit, and the lower casing) are separated. The electrodes are connected to the main unit when in use. The electrodes are generally hydrogel electrodes, which are not durable and needs to be replaced frequently. In the present disclosure, stainless steel metal electrodes are used, which do not need to be replaced since the stainless steel has high durability, wear resistance, as well as good electrical conductivity. In the present disclosure, the stainless steel electrodes are combined with the main unit and are injection-molded integrally by using the in-mold injection process, that is to say, the electrodes are embedded in the lower surfaces of the lower casing 4 and the support 7 to achieve the integration of the electrodes. In the prior art, the strap and the main unit are also separated, and the strap is generally made of a cloth material, which is not easy to clean, not durable, and needs to be replaced after a long time of use. In the present disclosure, soft rubber (such as TPE (Thermoplastic Elastomer), TPU (Thermoplastic Polyurethanes), or the like) is used as the material of the strap, which is durable, elastic, and stretchable, and can be molded into a desired shape. In one embodiment, the strap and the support are integrally molded by an overmolding process, so that the integration of the strap with the main unit is achieved.

Figure 3:
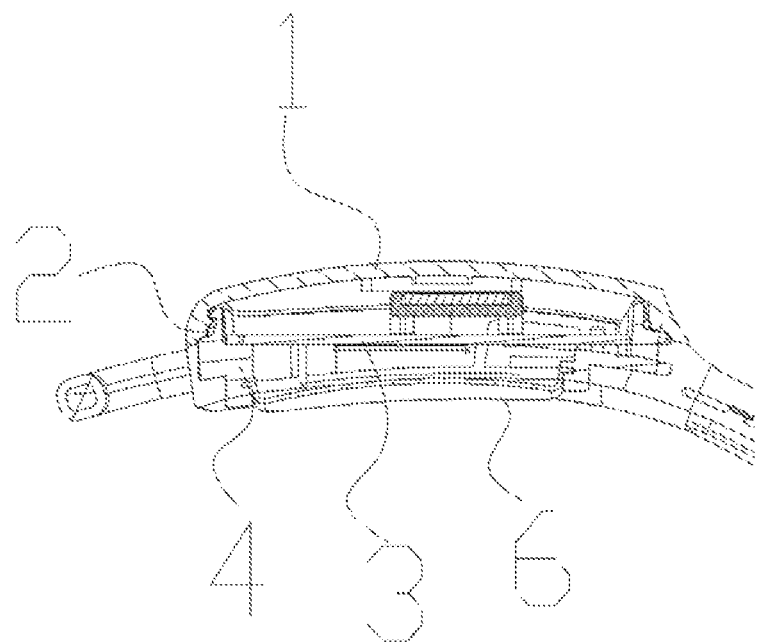
FIG. 3 is a view showing an overall waterproof design of a functional electrical stimulation therapeutic apparatus for foot drop according to an embodiment of the present disclosure.

As shown in FIG. 3, the waterproof ring 2 is located between the upper casing 1 and the lower casing 4, wherein the waterproof ring 2 is respectively in contact with side walls of the upper casing 1 and the lower casing 4 in an interference fit manner. Since the waterproof ring 2 is made of a soft rubber material such as silicone rubber which is elastic and deformable, the waterproof ring 2 is tightly pressed between the side walls of the uppercasing and the lower casing to achieve waterproofness of an assembly gap between the upper casing and the lower casing. The upper casing and the lower casing may be assembled and fixed by means of snap-fit, ultrasonic fusion joining (welding), or screwing. The large electrode 6 is located at the bottom of the lower casing 4 and is embedded in the outer surface of the lower casing 4 by using an in-mold injection process. The in-mold injection process enables the electrode to be brought into close contact with the lower casing.

Figure 4:
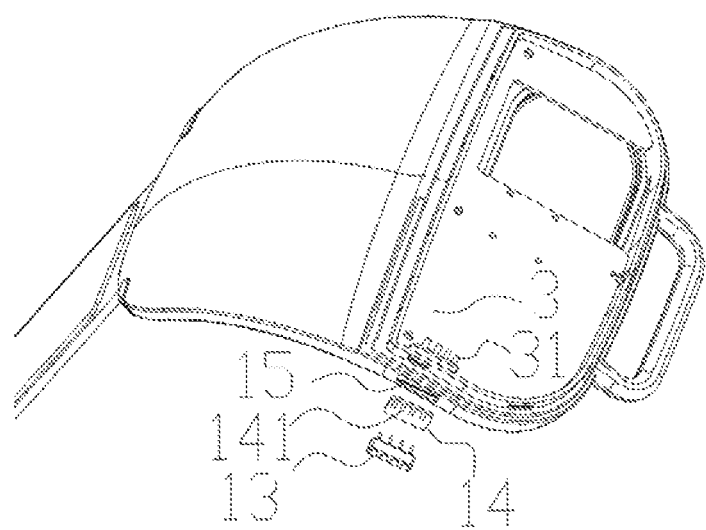
FIG. 4 is a schematic view of a waterproof structure for a communication interface of a functional electrical stimulation therapeutic apparatus for foot drop according to an embodiment of the present disclosure.

As shown in FIG. 4, the control circuit has a charging and communication interface. In general, this kind of interface is a MICRO USB or TYPE-C USB, but it is not waterproof. Therefore, a magnetic connector is used in the present disclosure. In other words, the charging interface of the control circuit is provided with a magnetic connector 13, wherein the magnetic connector 13 is located inside the lower casing 4 and is connected externally to a charging cable via a charging port 15 of the lower casing, and a terminal of the charging cable is attracted to the magnetic connector 13 to achieve the charging function. Since the magnetic connector is solid as a whole, the waterproofing function can be achieved during charging or communication. During manufacturing, an in-mold injection process is used in such a manner that the magnetic connector 13 is placed in a mold and the magnetic connector 13 is tightly enclosed by plastic forming the charging port 15 of the lower casing 4, thus there is no assembly gap between the magnetic connector and the charging port so as to prevent the entry of a liquid such as water. The charging port 15 is in a closed state when it is not charged at the usual time, that is to say, when it is idle.

In another embodiment, due to a limitation of structure space, the magnetic connector 13 cannot be directly connected with the control circuit 3 and needs to be connected indirectly thereto by using a connecting wire or directly welded thereto. An external additional connector must be a small and precise connector and has high cost, while a wire directly welded at a welding joint is easily broken and does not have high reliability. In the present disclosure, the magnetic connector 13 is directly welded to a magnetic connector circuit board 14, and then welded together with pads 31 on the control circuit 3 via pads 141 on the magnetic connector circuit board 14. The magnetic connector circuit board 14 is closely attached to the control circuit 3 on the main board, and the pads on the control circuit and the pads on the magnetic connector circuit board are put close to each other so as to be welded conveniently.

Figure 5:
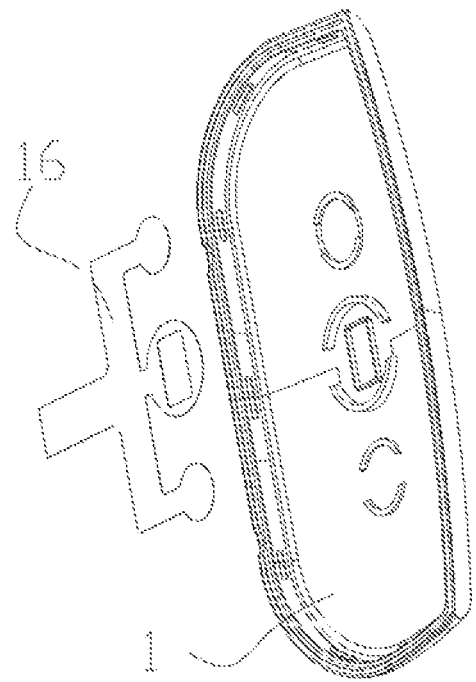
FIG. 5 is a schematic view of a waterproof structure for a button of a functional electrical stimulation therapeutic apparatus for foot drop according to an embodiment of the present disclosure.

As shown in FIG. 5, in one embodiment, a button is designed as a touch button, and a touch sensing portion thereof is implemented by a first flexible circuit board. The flexible circuit board 16 is closely attached to a limiting frame on an inner surface of the upper casing 1 by a 3M adhesive. In this way, a mechanical gap is avoided and a waterproofing effect is achieved. The upper casing 1 is a complete casing, which has a smooth outer surface on which a button mark is printed by silkscreen printing. In operation, upon a finger gently touches the button mark region on the outer surface of the upper casing 1, a corresponding circular sensing region of the flexible circuit board 16 can detect a related signal. The flexible circuit board 16 can sense a button pressing signal as long as the upper casing 1 has a casing thickness in the range of 1 to 2 mm.

Figure 6:
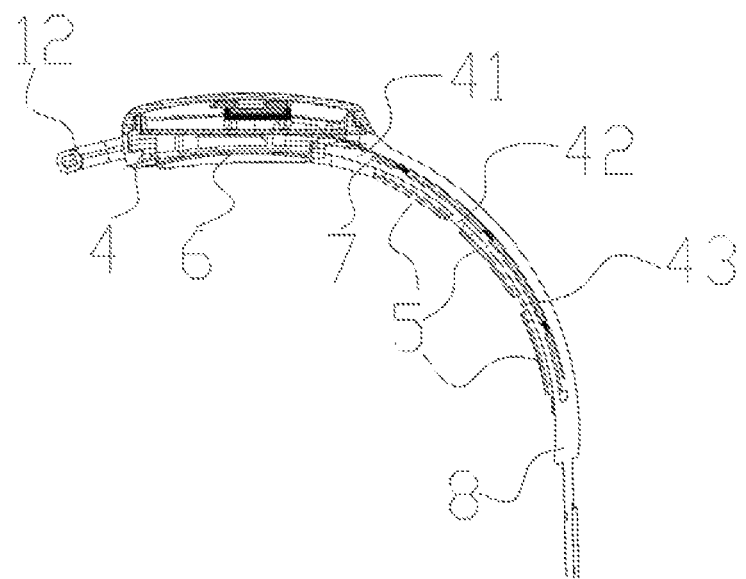
FIG. 6 is a structural schematic view of a support of a functional electrical stimulation therapeutic apparatus for foot drop according to an embodiment of the present disclosure.
Figure 8:
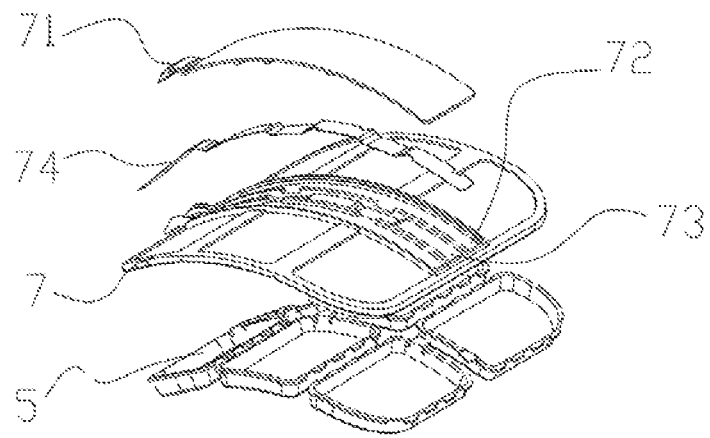
FIG. 8 is a schematic view of a combined structure of a sequence of small electrodes of a functional electrical stimulation therapeutic apparatus for foot drop according to an embodiment of the present disclosure.

As shown in FIG. 6 and FIG. 8, the large electrode 6 and the lower casing 4, and the sequence of small electrodes 5 and the support 7 are integrally injection-molded. The support 7 is made of a soft rubber material having a relatively high hardness. A first deformable region 41 is formed by a connecting portion between the lower casing 4 and upper electrodes among the sequence of small electrodes 5, a second deformable region 42 is formed by a connecting portion between the upper electrodes and intermediate electrodes among the sequence of small electrodes 5, and a third deformable region 43 is formed by a connecting portion between the intermediate electrodes and lower electrodes among the sequence of small electrodes 5, and the three deformable regions are all made of a soft rubber material, therefore the gaps between the three sets of sequences of small electrodes are bendable and deformable, so that the sequence of small electrodes 5 can be adapted to different diameters of legs of patients and brought into close contact with the skin of the leg. The soft rubber 8 tightly encloses the lower casing 4 and the large electrode 6, and the sequence of small electrodes 5 and the support 7, whereby the integration of the electrodes is formed.

Figure 7:
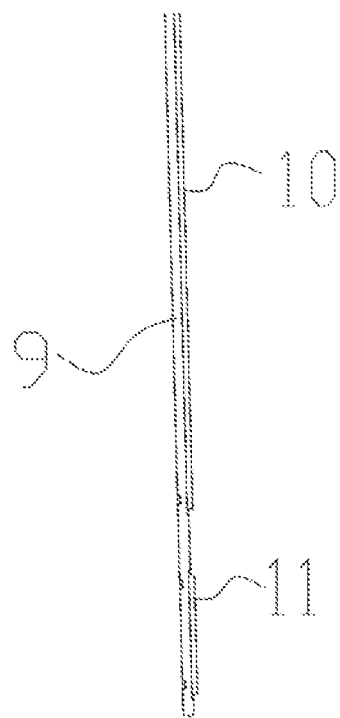
FIG. 7 is a structural schematic view of a strap of a functional electrical stimulation therapeutic apparatus for foot drop according to an embodiment of the present disclosure.

The soft rubber 8 of FIG. 6 extends downward to form the strap 9 of FIG. 7. The soft rubber may be TPE or TPU. A Velcro loop material 10 is fixed to an upper end of the strap 9 by a machine sewing process, a Velcro hook material 11 is fixed to a lower end of the strap 9 by the machine sewing process, and the strap 9 passes through a lug 12 of FIG. 6, and is folded back and then fixed by the Velcro. The length by which the strap is to be folded back is adjusted and fixed by the Velcro, so that the strap can be conveniently and reliably fixed to the leg.

As shown in FIG. 8, the sequence of small electrodes 5 is injection-molded integrally with the support 7, and the support 7 is made of a soft rubber material. An upper surface of the support 7 is provided with a cover slot 72 and a cover 71 for flexible circuit matched with the cover slot 72, and the cover 71 for flexible circuit is assembled to the cover slot 72 to form a closed space, which blocks an outer layer of soft rubber, so that the outer layer of soft rubber cannot enter the cover slot 72. The cover slot 72 is further provided therein with a wiring slot 73 in which a flexible circuit board 74 is mounted and the flexible circuit board 74 is freely bendable or stretchable in the wiring slot 73. Each single electrode of the sequence of small electrodes 5 has an inward bump, which is connected to the control circuit via a pad location of the flexible circuit board 74, so that the electrical connection between the sequence of small electrodes 5 and the flexible circuit board 74 can be achieved by a welding process.

Figure 9:
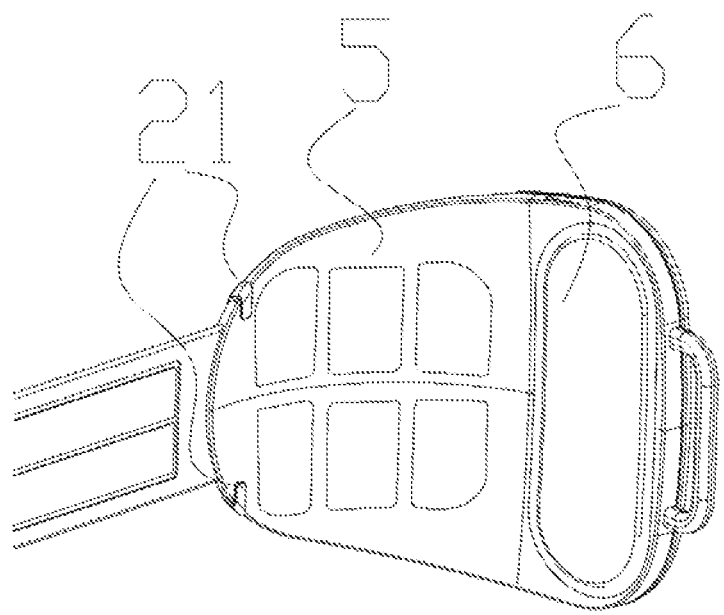
FIG. 9 is a schematic view showing an electrode structure of a functional electrical stimulation therapeutic apparatus for foot drop according to an embodiment of the present disclosure.
Figure 10:
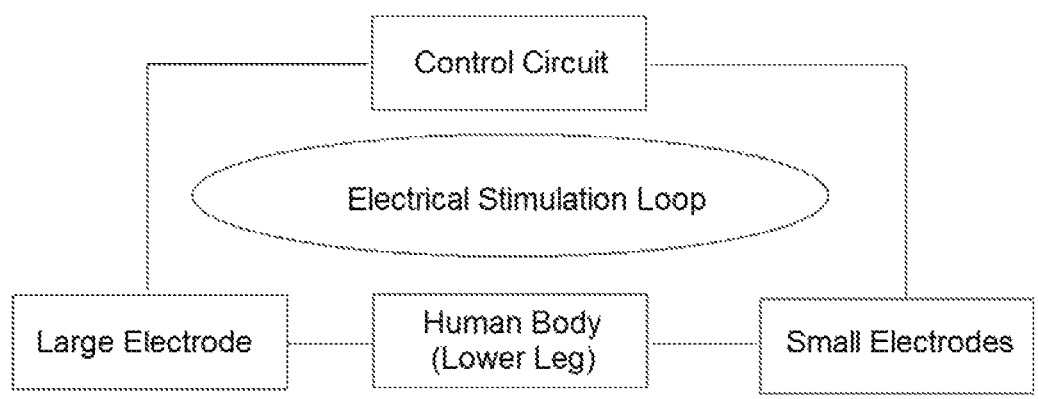
FIG. 10 is a schematic view of an electrical stimulation loop of a functional electrical stimulation therapeutic apparatus for foot drop according to an embodiment of the present disclosure.

As shown in FIG. 9, the sequence of small electrodes 5 and the large electrode 6 are arranged from left to right and are vertically symmetrical, and applicable to both left and right legs. The large electrode 6 has an oblong shape, and the small electrodes each have a rectangular shape. The small electrodes, the large electrode, the lower leg, and the electrical stimulation generating circuit constitute an electrical stimulation loop (circuit), as shown in FIG. 10. Without this loop, a stimulation current cannot be formed, and hence the functions of assisted walking and foot dorsiflexion cannot be achieved. In order to achieve the function of foot dorsiflexion, the large electrode must cover a junction of the common peroneal nerve, and the small electrodes must cover branches of the common peroneal nerve. According to the characteristics of the human body, a positioning point 21 is located at the rear end of the support 7, and is spaced apart from a nearest small electrode by 1 to 5 mm, and the large electrode 6 is spaced apart from a nearest small electrode by 10 to 15 mm. When in use, the positioning point 21 is aligned with the center of the lower edge of the kneecap, the large electrode 6 covers the junction of the common peroneal nerve junction, and the plurality of small electrodes 5 may cover the branches of the common peroneal nerve as much as possible without being brought into excessive contact with other nerves due to differences in branches of the common peroneal nerve of different people.

As one of the embodiments, a combination for a sequence of six small electrodes includes: any one electrode, any two electrodes, any three electrodes, any four electrodes, any five electrodes, or all the six electrodes.

As one of the embodiments, a combination for a sequence of eight small electrodes includes: any one electrode, any two electrodes, any three electrodes, any four electrodes, any five electrodes, any six electrodes, any seven electrodes, or all the eight electrodes. The combinations for other numbers of small electrodes can be deduced in the same manner.

An integrated waterproof design is used in the present disclosure, so that the electrodes and the strap are more durable and operated more simply; stainless steel electrodes are used in the present disclosure and do not need to be replaced since the stainless steel has high durability, wear resistance, as well as good electrical conductivity; and a sequence of electrodes are used in the present disclosure and can cover nerves and muscles of different groups of people.

While the embodiments of the present disclosure have been shown and described, it will be understood by those of ordinary skill in the art that a variety of changes, modifications, alternatives, and variations can be made to these embodiments without departing from the principle and spirit of the present disclosure, and the scope of the present disclosure is defined by the appended claims and their equivalents.

While the invention has been described in connection with various embodiments, it will be understood that the invention is capable of further modifications. This application is intended to cover any variations, uses or adaptations of the invention following, in general, the principles of the invention, and including such departures from the present disclosure as, within the known and customary practice within the art to which the invention pertains.

What is claimed is:

1. A functional electrical stimulation therapeutic apparatus for foot drop, comprising an upper casing, a waterproof ring, a control circuit, a lower casing, a support molded integrally with the lower casing, a sequence of small electrodes, and a large electrode, wherein the large electrode is injection-molded integrally with the lower casing, the large electrode is embedded in a surface of the lower casing by using an in-mold injection process, the sequence of small electrodes are injection-molded integrally with the support, the sequence of small electrodes are embedded in a surface of the support by using the in-mold injection process, the surfaces of the lower casing and the support are coated with a soft rubber, and the soft rubber is extended to form a strap, the large electrode and the lower casing which are integrally injection-molded and the sequence of small electrodes and the support which are integrally injection-molded are integrally injection-molded with the strap, the sequence of small electrodes and the large electrode are stainless steel metal electrodes, the lower casing is made of plastic, and the support is made of a soft rubber material having a relatively high hardness.

2. The therapeutic apparatus according to claim 1, wherein the control circuit is connected with a magnetic connector, the magnetic connector is disposed in the lower casing and connected with a charging cable via a charging port of the lower casing, and the charging port is in a closed state when it is idle.

3. The therapeutic apparatus according to claim 2, wherein the control circuit is connected with the magnetic connector via a magnetic connector circuit board.

4. The therapeutic apparatus according to claim 3, wherein the large electrode is configured to cover a junction of the common peroneal nerve, and the small electrodes are configured to cover branches of the common peroneal nerve.

5. The therapeutic apparatus according to claim 2, wherein the large electrode is configured to cover a junction of the common peroneal nerve, and the small electrodes are configured to cover branches of the common peroneal nerve.

6. The therapeutic apparatus according to claim 1, wherein an inner surface of the upper casing has a limiting frame, a first flexible circuit board is attached in the limiting frame, a button mark is provided at a location on an outer surface of the upper casing that is corresponding to the first flexible circuit board, and the first flexible circuit board is connected with the control circuit for transmitting, to the control circuit, information on a button pressing by a user.

7. The therapeutic apparatus according to claim 6, wherein the large electrode is configured to cover a junction of the common peroneal nerve, and the small electrodes are configured to cover branches of the common peroneal nerve.

8. The therapeutic apparatus according to claim 1, wherein the surface of the support is provided with a wiring slot in which a second flexible circuit board having pad locations is mounted, and the second flexible circuit board is connected with the control circuit via the pad locations; the sequence of small electrodes have bumps respectively connected with the pad locations and are connected with the control circuit via the bumps.

9. The therapeutic apparatus according to claim 8, wherein the surface of the support is provided with a cover slot and a cover for the second flexible circuit board matched with the cover slot, and the wiring slot is disposed in the cover slot.

10. The therapeutic apparatus according to claim 9, wherein the large electrode is configured to cover a junction of the common peroneal nerve, and the small electrodes are configured to cover branches of the common peroneal nerve.

11. The therapeutic apparatus according to claim 8, wherein the large electrode is configured to cover a junction of the common peroneal nerve, and the small electrodes are configured to cover branches of the common peroneal nerve.

12. The therapeutic apparatus according to claim 1, wherein the sequence of small electrodes comprises at least six small electrodes, the small electrodes are symmetrically distributed, the large electrode has an oblong shape, the small electrodes each have a rectangular shape, and are configured to form, with the control circuit, a human body, and the large electrode, an electrical stimulation loop.

13. The therapeutic apparatus according to claim 12, wherein the large electrode is configured to cover a junction of the common peroneal nerve, and the small electrodes are configured to cover branches of the common peroneal nerve.

14. The therapeutic apparatus according to claim 1, wherein a front end of the upper casing is provided with a lug, the strap is provided thereon with a Velcro loop material and a Velcro hook material, the Velcro loop material is fixed to an upper end of the strap by a machine sewing process, the Velcro hook material is fixed to a lower end of the strap by the machine sewing process, the strap passes through the lug and is folded back and then fixed by the Velcro, wherein the strap is folded back by a length which is adjusted and fixed by the Velcro.

15. The therapeutic apparatus according to claim 14, wherein the strap is made of TPE (Thermoplastic Elastomer) or TPU (Thermoplastic Polyurethanes).

16. The therapeutic apparatus according to claim 14, wherein the large electrode is configured to cover a junction of the common peroneal nerve, and the small electrodes are configured to cover branches of the common peroneal nerve.

17. The therapeutic apparatus according to claim 1, wherein the large electrode is configured to cover a junction of the common peroneal nerve, and the small electrodes are configured to cover branches of the common peroneal nerve.

18. The therapeutic apparatus according to claim 1, wherein a rear end of the support has a positioning point, the positioning point is spaced apart from a nearest small electrode by 1 to 5 mm, and the large electrode is spaced apart from a nearest small electrode by 10 to 15 mm.

* * * * *